United States Patent [19]

Glisson

[11] Patent Number: 4,858,601
[45] Date of Patent: Aug. 22, 1989

[54] ADJUSTABLE COMPRESSION BONE SCREW

[76] Inventor: Richard R. Glisson, 311 S. LaSalle St. #34K, Durham, N.C. 27705

[21] Appl. No.: 200,054

[22] Filed: May 27, 1988

[51] Int. Cl.$^4$ .......................... A61F 5/04; F16B 35/00
[52] U.S. Cl. .............................. 128/92 R; 128/922 W; 128/92 YR; 128/92 YE; 411/389
[58] Field of Search ....... 128/92 ZZ, 92 ZW, 92 YU, 128/92 YK, 92 YR, 92 YE, 92 R, 92 VD, 92 YU; 411/383, 384, 389, 395

[56] References Cited

U.S. PATENT DOCUMENTS

| 188,668 | 3/1877 | Pleukharp | 411/389 |
|---|---|---|---|
| 1,749,547 | 3/1930 | Ruddy | 411/389 |
| 3,051,169 | 8/1962 | Grath | 128/92 R |
| 3,408,887 | 11/1968 | Villo | 411/389 |
| 3,424,212 | 1/1969 | Kemper | 411/395 |
| 3,716,051 | 2/1973 | Fischer | 128/92 R |
| 4,013,071 | 3/1977 | Rosenberg | 128/92 R |
| 4,052,988 | 10/1977 | Doddi et al. | 128/335.5 |
| 4,175,555 | 11/1979 | Herbert | 128/92 |
| 4,212,294 | 7/1980 | Murphy | 128/92 R |
| 4,227,518 | 10/1980 | Aginsky | 128/92 R |
| 4,237,875 | 12/1980 | Termanini | 128/92 R |
| 4,379,451 | 4/1983 | Getscher | 128/92 R |
| 4,432,358 | 2/1984 | Gixel | 128/92 R |
| 4,453,539 | 1/1984 | Raftopoulos et al. | 128/92 R |
| 4,484,570 | 11/1984 | Sutter et al. | 128/92 R |
| 4,530,355 | 7/1985 | Griggs | 128/92 R |
| 4,574,795 | 3/1986 | Georges | 128/92 R |
| 4,640,271 | 2/1987 | Lower | 128/92 YE |

Primary Examiner—Robert A. Hafer
Assistant Examiner—Michael Brown
Attorney, Agent, or Firm—Robert G. Rosenthal

[57] ABSTRACT

An adjustable compression bone screw that has a shaft having first and second sections each with an external screw thread that may be rotated as a unit or independently. The screw includes means adapted to receive a first driving tool for driving the shaft as unit and further adapted to receive a second driving tool for rotating the second section independently of the first section.

9 Claims, 3 Drawing Sheets

ADJUSTABLE COMPRESSION BONE SCREW

FIELD OF THE INVENTION

This invention relates to the field of orthopedic surgery wherein two pieces of a fractured bone must be joined together in compression for optimum healing.

BACKGROUND OF THE INVENTION

In orthopedic surgery it is common to rejoin broken bones. However, in most situations where cross-fixation of the bone fragments is required, the success of the surgical procedure depends to a large extent on the degree of compression that can be achieved between the bone fragments. More specifically, if the surgeon is unable to bring the bone fragments in close contact with each other, there will exist a space or void into which the bone tissue must grow before the healing process is complete. Thus, the greater the distance between the bone fragments, the slower the healing process. In addition, the healing process can be retarded by any relative movement or shifting of the bone fragments which disturbs the bone tissue that has been laid down.

Screws commonly used in fracture fixation are of the lag type, and comprise a threaded leading end and an enlarged head incorporating a means to engage a driving tool at the trailing end. Situations often arise in which the presence of a screw head has a deleterious effect on the outcome of the repair, specifically in cases where the screw must be inserted in or near a skeletal joint or where inadequate bone stock is available to allow countersinking of the screw head.

In response to the above-noted problems, attempts have been made to improve upon the lag type screw. An apparatus is described in U.S. Pat. No. 4,175,555 issued Nov. 27, 1979 to Timothy J. Herbert which discloses a bone screw capable of connecting two bone fragments under compression and which lacks a conventional screw head, allowing complete burial of the device in the bone substance. This is accomplished by a screw which is threaded at its leading and trailing ends. The threads are like-handed, but are of unequal pitch. More specifically, the pitch of the thread at the leading end exceeds the pitch at the trailing end, thus causing the leading end of the screw to advance at a slightly faster rate than the trailing end which causes the bone fragments to be brought under some degree of compression.

While somewhat effective, the Herbert screw is not without its inherent drawbacks. For example, as a result of the relatively small difference in the thread pitch between the leading and trailing threads, the screw has a very limited ability to draw together bone fragments that are not already intimately opposed upon screw insertion. In addition, since the pitch of the leading and trailing threads differs, the outside diameter of the leading threads must be smaller than the core or root diameter of the trailing threads to prevent binding. Thus, the leading end of the screw has a weaker purchase on the bone than does the trailing end as the force required to pull a screw out of its bore is a function of thread diameter.

An additional drawback of the Herbert screw is that it lacks the "feel" for tightness available to the surgeon in a conventional lag screw. When the Herbert screw is employed in a repair, the bore for the trailing threads is not tapped and can not be tapped because of thread synchronization problems. Therefore, the surgeon feels only the resistance due to the trailing threads penetrating the bone, thereby introducing the possibility of sub-optimal repairs.

It is accordingly an object of the present invention to provide a bone screw wherein a first and a second bone fragment can be connected under compression.

Another object of the invention is to provide a bone screw wherein a first and a second bone fragment can be connected under adjustable compression or adjustable distraction.

A further object of the invention is to provide a bone screw wherein thread pullout strength on either side of the fracture line is equalized.

A still further object of the invention is to provide a bone screw wherein the surgeon will have the "feel" of a conventional lag screw.

A still further object of the present invention is to provide a bone screw with adjustable compression that yields compressive force substantially equal to that of a conventional lag screw.

A still further object of the present invention is to provide a bone screw wherein the screw is completely buried within the bone.

SUMMARY OF THE INVENTION

The benefits and advantages of the present invention are achieved in a bone screw for connecting first and second bone fragments together. The screw comprises a shaft having a first section and a second section that are rotatable independently of each other. The first section includes a first external screw thread and the second section includes a second external screw thread. The screw also includes means associated with the second section that are adapted to receive a first driving tool for driving the shaft as a unit and further adapted to receive a second driving tool for rotating the second section independently of the first section. When the screw is engaged by the first driving tool it is rotated as a unit through the first and second bone fragments with the first and second sections being driven into the respective first and second bone fragments. Furthermore, when the screw is engaged by the second driving tool, the second section rotates independently of the first section. Upon rotation of the second section of the screw in a direction opposite to the direction of rotation for driving the screw as a unit, the second bone fragment is drawn towards and closely adjacent to the first bone fragment.

BRIEF DESCRIPTION OF THE DRAWINGS

Some of the features and advantages of the invention having been briefly stated, others will appear from the detailed description which follows, when taken in connection with the accompanying drawings, in which.

DETAILED DESCRIPTION OF THE ILLUSTRATED EMBODIMENT

While the present invention will be described more fully hereinafter with reference to the accompanying drawings, in which a particular embodiment is shown, it is to be understood at the outset that persons skilled in the art may modify the invention herein described while still achieving the favorable results of this invention. Accordingly, the description which follows is to be understood as a broad teaching disclosure directed to persons of skill in the appropriate arts and not as limiting upon the present invention.

Figure 1:
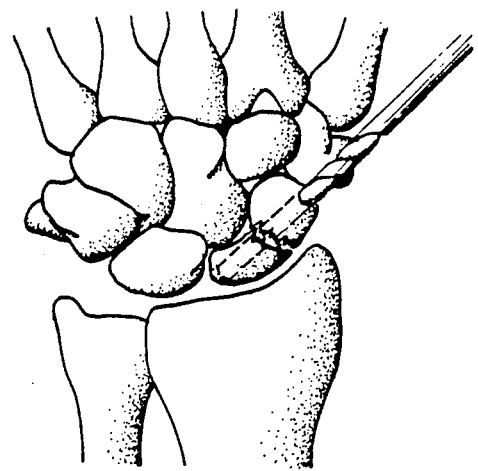
FIG. 1 is a side view of a fractured scaphoid bone being drilled in preparation for tapping.
Figure 2:
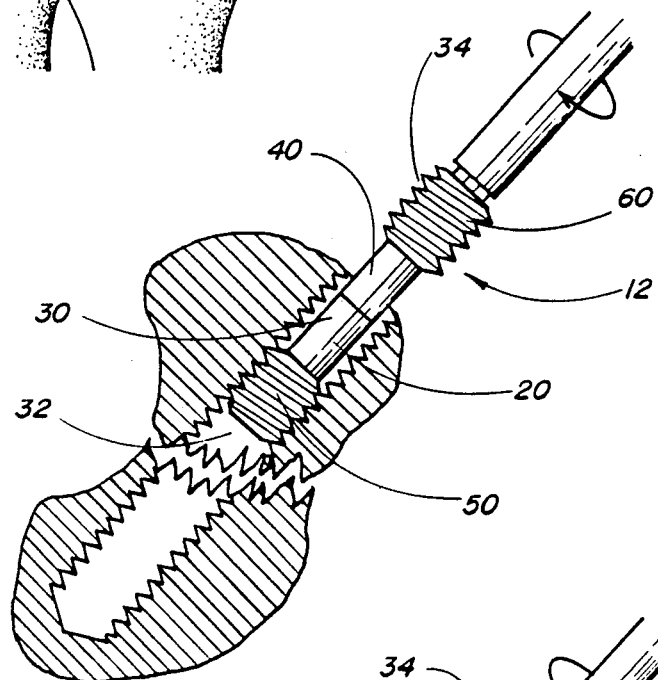
FIG. 2 is a cross section of a fractured scaphoid showing the bone screw of the present invention being inserted therein by a first driving tool that rotates the screw in a first direction.
Figure 3:
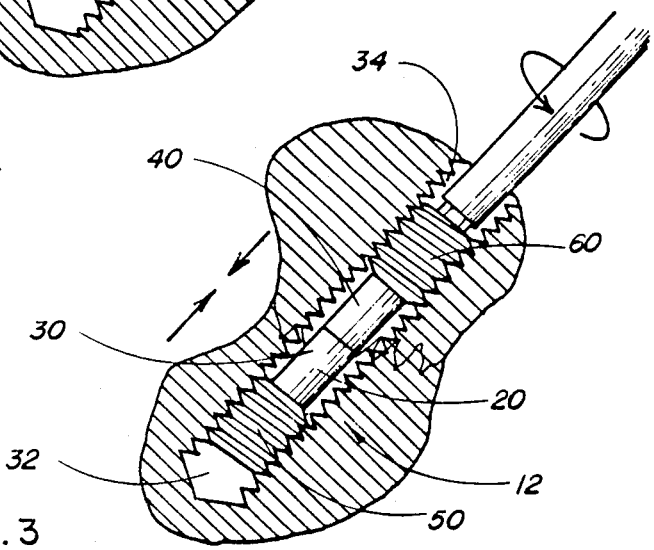
FIG. 3 is a cross section of a fractured scaphoid showing the bone screw of the present invention fully inserted therein and wherein the trailing end of the screw is rotated by a second driving tool in the direction opposite the first direction of rotation so as to bring the bone fragments into compression.
Figure 4:
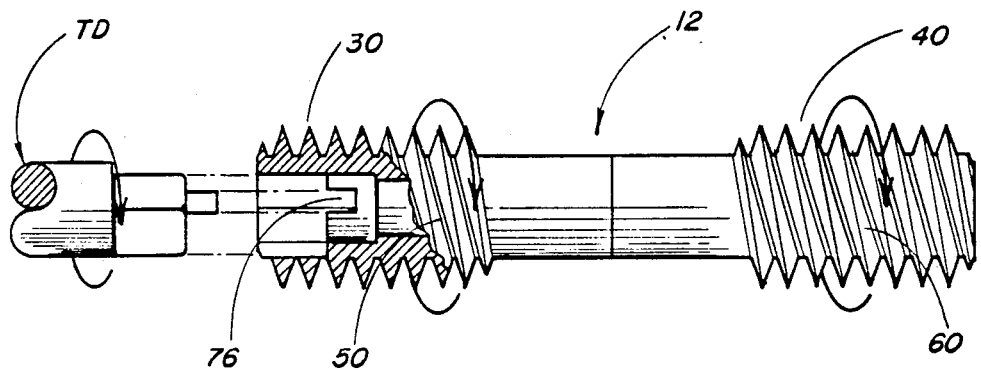
FIG. 4 is a side view, partially broken away, of the bone screw of the present invention showing the screw being rotated as a unit with the first driving tool.
Figure 5:
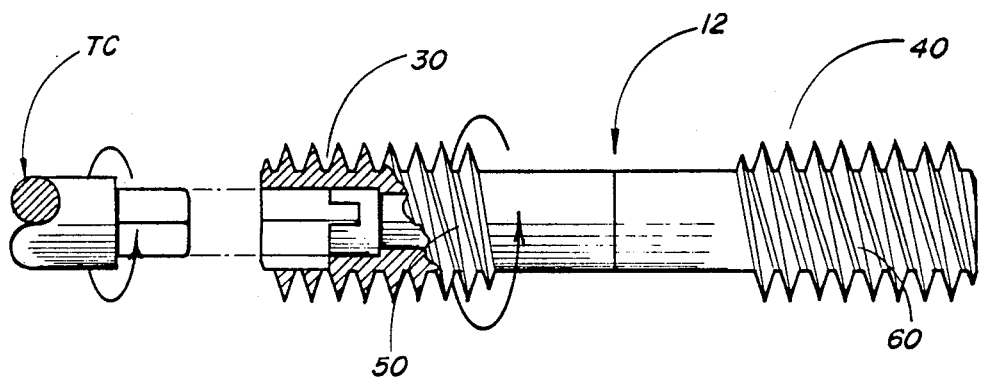
FIG. 5 is a side view, partially broken away, of the bone screw of the present invention showing the trailing end being rotated by a second driving tool.

Referring now more particularly to the drawings and specifically to FIGS. 2 and 3, a bone screw according to the present invention is there illustrated being inserted into a first and a second bone fragments.

The bone screw generally indicated at 12 comprises a shaft 20 having a first section 30 and a second section 40. The shaft 20 is cylindrical and includes a bore 22 extending along its longitudinal axis through the first and second sections 30, 40. The screw 12 may be fabricated from any biocompatible material such as stainless steel, ceramics and the like. In addition, it will be appreciated that the screw 12 can be made from biodegradable materials having a life engineered to correlate to the approximate healing time for a given fracture.

Figure 8:
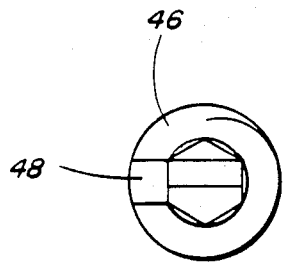
FIG. 8 is a top view of the bone screw of the preset invention.
Figure 9:
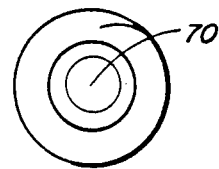
FIG. 9 is a bottom view of the bone screw of the present invention.

The screw 12 includes a leading end portion 32 and a trailing end portion 34. A first external screw thread 50 is located near the leading end portion 32 of the first section 30. The second section 40 of shaft 20 includes a second external screw thread 60 located near the trailing end portion 34. The second section 40 further includes a hexagonal socket 46 with one portion of its side wall being cut out and defining a notch 48 therein (as best shown in FIG. 8).

In the illustrated embodiment, the first and second screw threads 50, 60 are like handed and of equal pitch and diameter. Additionally, the screw threads are positioned on the shaft so that the second threads follow the first threads in thread synchronization when the shaft is engaged by the first driving tool TD as will be explained in greater detail hereinbelow.

Figure 6:
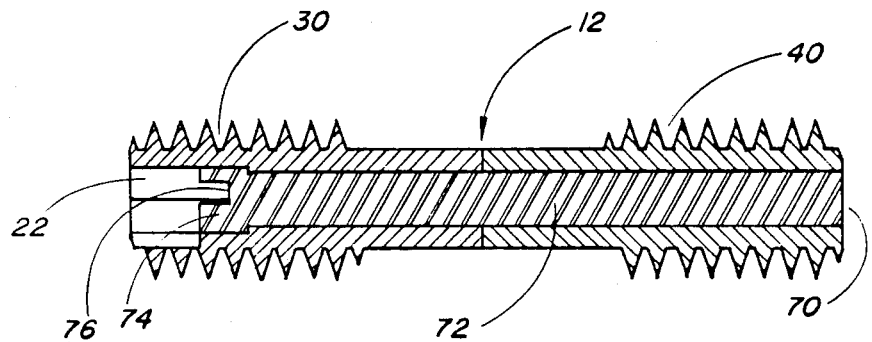
FIG. 6 is a side view taken in section of the bone screw of the present invention.
Figure 7:
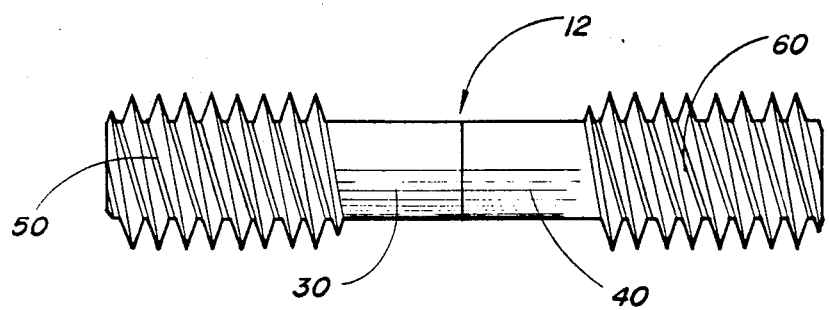
FIG. 7 is a side view of the bone screw of the present invention.
Figure 10:
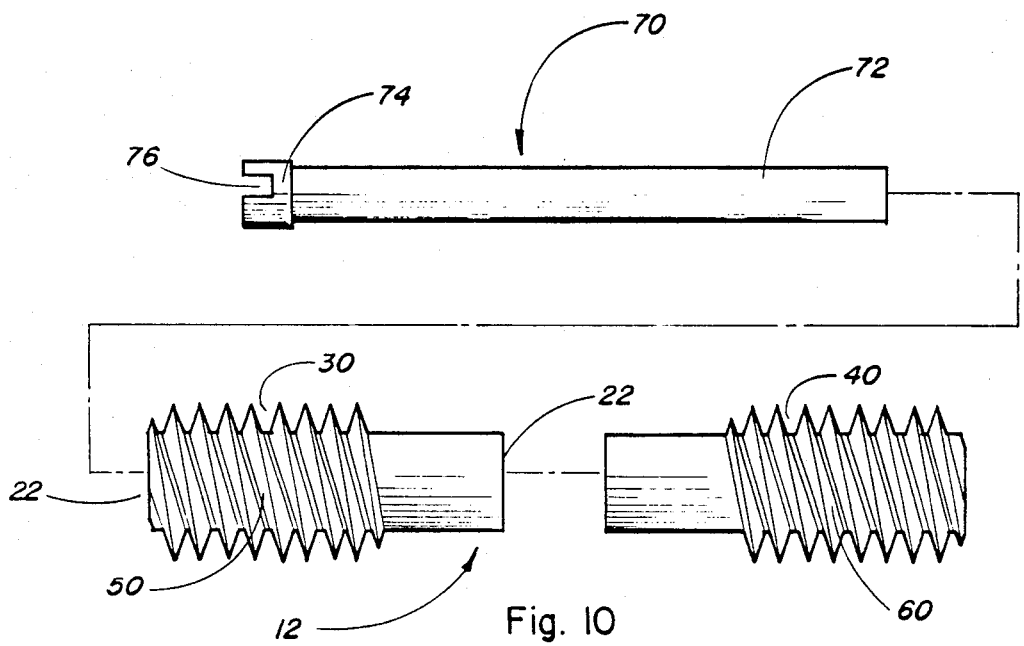
FIG. 10 is an exploded side view of the bone screw of the present invention showing its component parts.

The screw 12 also includes a spindle 70 that comprises an elongated body 72 having a head 74 at one of its ends. The head 74 is slightly larger in diameter than the body 72 and includes a transverse slot 76. The spindle 70 is adapted to be received within the bore 22 of the first and second sections 30, 40 (as best shown in FIGS. 6 and 10). During fabrication of the screw, the spindle 70 and the first section 30 are joined together by suitable means, such as solder. As a result, the first section 30 is free to rotate about the head of the spindle 70.

The screw 12 also includes means adapted to receive a first driving tool TD for driving the screw 12 as a unit and further adapted to receive a second driving tool TC for rotating the second section 40 independently of the first section 30. The means adapted to receive the first driving tool TD for driving the screw as a unit includes the transverse slot 76, the hexagonal socket 46, and the notch 48. It will be noted that the transverse slot 76 is positioned off center in the illustrated embodiment (as best shown in FIGS. 4 through 6 and 8) and is, therefore, properly engagable by the first driving tool TD in one orientation only. Similarly, as previously mentioned, the trailing end portion 34 also includes hexagonal socket 46 with a cutout portion defining a notch 48 in the side wall. Thus, the second section is also engagable in one orientation only by the first driving tool TD. As a result, when the screw is rotated as a unit by the first driving tool TD the first and second external threads 50, 60 are necessarily in thread synchronization which enables the screw to be inserted into the bone as a unit without cross-threading or binding of the second external thread as it enters the bore.

The screw also includes means adapted to receive a second driving tool TC for rotating the second section 40 independently of the first section 30 that in the illustrated embodiment takes the form of the socket described above, but aforementioned transverse slot in spindle 70 and notch 48 are not engaged by the second driving tool.

In operation, the bone fragments to be joined together are approximated and then drilled and tapped. Then the first driving tool TD is inserted into the trailing end of the second section 40 so as to engage transverse slot 76 and the notch 48 thus locking the first and second sections 30,40 together so that the shaft 20 rotates as a unit and the first and second threads 50,60 are in thread synchronization. The surgeon then rotates the screw 12 which is advanced as a unit through the first and second bone fragments until the first and second sections 30,40 are received in the respective first and second bone fragments and the entire device is buried within the bone substance.

Then the surgeon removes the first driving tool TD and inserts the second driving tool TC into the hexagonal socket 46. The second driving tool TC engages only the second section 40 and the first section 30 is left at rest in the first bone fragment. It will be noted that at this point in the procedure there will still exist some degree of gap between the bone fragments. The gap is narrowed by employing the second driving tool TC to rotate only the second section 40 in a direction opposite to the direction of rotation wherein the screw 12 was driven into the bone fragments. Since the first section 30 is substantially fixed within the first fragment, the second bone fragment must necessarily be drawn towards and more closely adjacent and into compression with the first bone fragment and the gap between them is narrowed. Thus, the surgeon is provided with a mechanism that allows the first and second bone fragments to be brought adjustably into compression. On the other hand, should distraction be required, the reader will note that this can also be easily achieved with the present invention.

The foregoing embodiments and examples are to be considered illustrative, rather than restrictive of the invention, and those modifications which come within the meaning and range of equivalence of the claims are to be included therein.

That which is claimed is:

1. A bone screw for connecting first and second bone fragments together, comprising:
   (a) a shaft having a first section and a second section rotatable independently of each other;
   (b) a first external screw thread on said first section;
   (c) a second external screw thread on said second section;
   (d) means associated with said second section adapted to receive a first driving tool for driving the screw as a unit and further adapted to receive a second driving tool for rotating the second section independently of the first section whereby upon rotation of the shaft by the first driving tool, the screw is advanced as a unit through the first and second bone fragments with the first and second sections being received in the respective first and second bone fragment and when the second section is rotated in a direction opposite to the direction of rotation for driving the screw as a unit into the first and second bone fragments, the second bone fragment is drawn towards and closely adjacent to the first bone fragment.

2. The bone screw according to claim 1 wherein said shaft is adapted to be embedded completely within the bone.

3. The bone screw according to claim 1 wherein the first and second sections are in thread synchronization when the means for driving the screw as a unit is engaged by the first driving tool.

4. The bone screw according to claim 1 wherein the means for driving the screw as a unit further includes a spindle projecting into said second section and wherein said spindle includes a transverse slot associated with the portion that projects into the second section and wherein the trailing end portion of said second section includes a hexagonal socket including a cutout portion in its side wall.

5. The bone screw according to claim 1 wherein the means for driving the shaft as a unit comprises:
   (a) a transverse slot in the trailing end portion of said first section; and
   (b) a cutout portion in the side wall of the second trailing end portion of said second section.

6. The bone screw according to claim 5 wherein said transverse slot is positioned off center so that the first driving tool can only engage said transverse slot in one orientation, whereby the first and second external threads are locked in thread synchronization when said driving means is engaged by the first driving tool.

7. The bone screw according to claim 1 wherein said bone screw is of a biodegradable material.

8. An apparatus for connecting first and second bone fragments together, comprising:
   (a) a screw comprising:
      i. a shaft having a first and a second section rotatable independently of each other;
      ii. a first external screw thread on said first section;
      iii. a second external screw thread on said second section;
      iv. means associated with said second section adapted to receive a first driving tool for driving the screw as a unit through the first and second bone fragments with the first and second sections being received in the respective first and second bone fragments and further adapted to receive a second driving tool for rotating said second section independently of said first section;
   (b) a first driving tool comprising:
      i. an elongate shaft having a first driving means located proximate one end thereof; said first driving means adapted to drive the screw as a unit;
   (c) a second driving tool comprising:
      i. an elongate shaft having a second driving means located proximate one end thereof; said second driving means adapted to engage only the trailing end of said screw.

9. A method of connecting a first and second bone fragment together in compressive engagement comprising the steps of:
   rotating in a first direction a bone screw having a first section and a second section with a first external screw thread on the first section and a second external screw thread on the second section, and where the second section is adapted to receive a first driving tool for rotating the first and second sections together to advance the bone screw as a unit so that the first section is positioned in the first bone fragment and the second section is positioned in the second bone fragment; and
   rotating in the opposite direction the second section independent of the first section with a second driving tool to move the second bone fragment into proximate compressive engagement with the first bone fragment.

* * * * *